United States Patent [19]

Katsumi

[11] Patent Number: 5,135,933

[45] Date of Patent: Aug. 4, 1992

[54] METHOD FOR TRANSPLANTATION OF FERTILIZED OVA

[75] Inventor: Akira Katsumi, Yamagata, Japan

[73] Assignee: Fujisawa Pharmaceutical Company, Ltd., Osaka, Japan

[21] Appl. No.: 525,050

[22] Filed: May 18, 1990

[30] Foreign Application Priority Data

May 25, 1989 [JP] Japan ................................ 1-133927
Dec. 29, 1989 [JP] Japan ................................ 1-343985

[51] Int. Cl.$^5$ ...................... A61K 31/44; A61K 31/40
[52] U.S. Cl. .................................... 514/291; 514/408
[58] Field of Search ............... 514/408, 427, 428, 291

[56] References Cited

U.S. PATENT DOCUMENTS 3,483,294 12/1969 Ohki et al. .......................... 514/408

FOREIGN PATENT DOCUMENTS 1-906630 7/1989 Japan .
708370 5/1954 United Kingdom .
968776 9/1964 United Kingdom .

OTHER PUBLICATIONS

Chemical Abstracts (63:18034b) 1965.
Chemical Abstracts (3489a) 1966.
Patent Abstracts of Japan, vol. 13, No. 487, (C-649) [3835], Nov. 6, 1989.
Arzneim.-Forsch., vol. 26, No. 7, 1976, pp. 1359-1361; R. Bauer et al.: "Cholinerge Kontraktion der Harnblase des Hundes durch elektrische Reizung des N. pelvicus und der Nerven in den Ligamenta lateralia und ihre Beeinflussung durch Atropin und Scopolaminbutylbromid".
Nippon Yakurigaku Zasshi, vol. 69, No. 2, 1973, pp. 257-267; T. Wakabayashi et al.: "Pharmacological effects of butoxybenzyl hyoscyamine bromide on isolated smooth muscle organs in animals".
Arznei.-Forsch., vol. 17, No. 7, 1967, pp. 882-885; C. Vallve: "Die wirkung von Spasmolytica auf die mechanische und elektrische Aktivitaet des isolierten Rattenuterus".
ACTA Physiologica Scandinavica, vol. 124, No. 3, Jul. 1985, pp. 429-436; M. Stjernquist et al.: "Cholinergic and adrenergic neural control of smooth muscle function in the non-pregnant rat uterine cervix".
ACTA Physiologica Scandinavica, vol. 484, suppl., 1980, pp. 1-24, Stockholm, SW; M. Hammarstroem: "Uterine secretomotor innervation".
Folia Medica, vol. 24, No. 1, 1982, pp. 31-36; A. Tanev et al.: "The effect of some clinically used spasmolytics on the uterus and other smooth muscles".

Primary Examiner—Frederick E. Waddell
Assistant Examiner—K. Weddington
Attorney, Agent, or Firm—Oblon, Spivak, McClelland, Maier & Neustadt

[57] ABSTRACT

A method for transplanting fertilized ova comprising administering a parasympatholytic agent such as prifinium bromide or scopolamine butylbromide to a recipient animal and then transplanting fertilized ova in the animal.

3 Claims, No Drawings

METHOD FOR TRANSPLANTATION OF FERTILIZED OVA

This invention relates to a method of transplanting fertilized ova of cattle or the like and a drug used therein. More particularly, the invention relates to a method of transplanting fertilized ova which comprises transplanting fertilized ova after administration of a parasympatholytic agent such as prifinium bromide or scopolamine butylbromide to recipient cattle or the like and a supportive drug for transplantation of fertilized ova which is used in the method. The invention finds application in the field of animal production.

For the purpose of producing improved species of beef cattle or the like and reducing the production cost thereof, the technique of transplanting fertilized ova is spreading.

For the transplantation of fertilized ova, there are two approaches, namely surgical transplantation which involves a surgical operation and a non-surgical transplantation using a local anesthetic, e.g. lidocaine.

Prifinium bromide, one of the parasympatholytics used in this invention, is known by the chemical name of "1-1-diethyl-3-(diphenylmethylene)-2-methylpyrrolidinium bromide" and has been used as a veterinary drug. Among the known indications of this drug are relief of the increased tone and spasm, increased motor function and pain of the alimentary canal associated with gastrointestinal diseases (forestomach diseases such as ruminal impaction, and gastrointestinal diseases such as gastroenteritis and gastrointestinal catarrh and colic) and relief of the increased tone and spasm and pain of the urinary tract associated with urolithiasis.

Scopolamine butylbromide has been used as a drug for humans as well. The known indications include relief of spasm and increased motor function in gastric/duodenal ulcer, esophagospasm, pylorospasm, gastritis, enteritis, intestinal colic, spastic constipation, functional diarrhea, cholecystitis, cholangitis, cholelithiasis, biliary dyskinesia, sequelae to gastrectomy/cholecystectomy, urinary stone, cystitis, urethrospasm/cystospasm due to insertion of an instrument, dysmenorrhea and spasm of the lower uterus at delivery and pretreatment for roentgenography and for endoscopy of the digestive tract.

Of the methods for transplanting fertilized ova, surgical transplantation achieves a high conception rate but is disadvantageous in that it is laborious and time-consuming.

Non-surgical transplantation does not take as much time but has the disadvantage of low conception rates. As to the non-surgical transplantation method, the procedure under anesthesia with a local anesthetic, such as lidocaine, has been broadly used but since the procedure relaxes the sphincter ani as well as the rectal wall, the air finds its way into the rectum when the hand is inserted for transplantation. This air expands the rectum to interfere with the transplantation procedure and, hence, acts as a factor in reducing the conception rate.

The inventor of this invention conducted an assiduous research for improving the conception rate following fertilized ovum transplantation in an expedient manner and found that the administration of a parasympatholytic agent such as prifinium bromide or scopolamine butylbromide to recipient cattle relaxes not only the rectal wall but also the uterine wall without accompanying a relaxation of the sphincter ani, with the result that the transplanting instrument can be inserted deeper into the uterus to help achieve a remarkable improvement in conception rate. This invention is predicated on the above finding.

The method of this invention is applicable to cattle, e.g. beef cattle and dairy cattle, swine, horses and so on.

Examples of the parasympatholytics to be used in this invention include prifinium bromide, scopolamine butylbromide, atropine and so on.

The administration and dosage of the parasympatholytic agent are not critical but can be chosen in accordance with the particular agent to be employed. Generally, however, satisfactory results are obtained when prifinium bromide is used in an intravenous dose of 30 to 50 mg/aminal or scopolamine butylbromide is used in an intravenous dose of 80 to 140 mg/animal to recipient cattle.

When prifinium bromide is used at ovum collection as well, satisfactory results are assured by intravenous injection of 50-100 mg/animal to donor cattle.

The technique for transplantation of fertilized ova is the same as that used conventionally but it is preferable to go through the transplantation procedure while the rectal and uterine walls remain relaxed after drug administration.

EXAMPLES

EXAMPLE 1

Prifinium bromide (7.5 g) was dissolved in distilled water for injection (1,000 ml) and the resultant aqueous solution was filled, in 5 ml portions, into ampoules, which were then sealed.

The injection thus prepared was used in Example 3.

Example 2

Scopolamine butylbromide (2.0 g) was dissolved in distilled water for injection (100 ml) and the resultant aqueous solution was filled, in 5 ml portions, into ampoules, which were then sealed.

The injection thus prepared was used in Example 4 as below.

Example 3

In donor cattle at collection of ova, comparison was made a lidocaine caudal epidural anesthesia group consisting of 5 Holstein and 10 Japanese Black cattle (a total of 15 animals) and a prifinium bromide intravenous injection group consisting of 1 Holstein and 6 Japanese Black cattle (a total of 7 animals). A similar comparison was made in recipient cattle at transplantation using 60 animals for lidocaine caudal epidural anesthesia and 23 animals for prifinium bromide intraveous injection.

The dose for donor cattle at ovum collection was 75 mg/animal (10 ml) intravenously and the dose for recipient cattle at transplantation was 37.5 mg/animal (5 ml) intravenously.

Immediately after intravenous injection of prifinium bromide, arrest of rectal peristalsis, relaxation of the rectal wall and relaxation of the wall of the uterus were found in remarkable degrees in both donor and recipient cattle. The duration of action in donor cattle was 59.6 minutes on the average. The average duration of action in recipient cattle was 28.4 minutes.

The results are shown in the following table.

|  |  | Number of trans- planted cattle | Number of impreg- nated cattle | Con- ception rate |
| --- | --- | --- | --- | --- |
| Epidural anesthesia with lidocaine | One fresh ovum | 4 | 1 | 25.0% |
|  | Two fresh ova | 8 | 4 | 50.0% |
|  | One frozen ovum | 39 | 10 | 25.6% |
|  | Two frozen ova | 9 | 4 | 44.4% |
|  | Total | 60 | 19 | 31.7% |
| Intravenous injection of prifinium bromide | One fresh ovum | 2 | 2 | 100.0% |
|  | Two fresh ova | 1 | 0 | 0.0% |
|  | One frozen ovum | 14 | 8 | 57.1% |
|  | Two frozen ova | 6 | 6 | 100.0% |
|  | Total | 23 | 16 | 69.6% |

Example 4

Scopolamine butylbromide 100 mg/animal (5 ml), instead of prifinium bromide 37.5 mg/animal (5 ml) in Example 3, was injected intravenously to recipient cattle at transplantation and fertilized ova were transplanted in the same manner as n Example 3. The fertilized ova were obtained in the same manner as in Example 3.

The results are shown in the following table.

|  |  | Number of trans- planted cattle | Number of impreg- nated cattle | Con- ception rate |
| --- | --- | --- | --- | --- |
| Scopolamine butyl- bromide | One fresh ovum | 2 | 1 | 50.0% |
|  | Two fresh ova | — | — | — |
|  | One frozen ovum | 4 | 4 | 100.0% |
|  | Two frozen ova | 1 | 0 | 0.0% |
|  | Total | 7 | 5 | 71.4% |

The conception rate after transplantation of fertilized ova in accordance with this invention is higher than 50%, which is said to be "a parameter of fertilized ovum transplantation technology which is expected to be achieved in the near future by the non-surgical method" and even higher than 60% which is said to be "a parameter of fertilized ovum transplantation technology which is desirably achieved" (Chikusan-no-kenkyu 42(11), -14) and, therefore, this invention is believed to provide a far-reaching benefit to the animal industry.

I claim:

1. A method for transplanting fertilized ova comprising:
   intravenously administering a parasympatholytic agent in an amount which relaxes the rectal wall without substantially relaxing the sphincter ani to a recipient animal and, then, transplanting fertilized ova in the animal.

2. A method for transplanting fertilized ova as claimed in claim 1 wherein said parasympatholytic agent is prifinium bromide.

3. A method for transplanting fertilized ova as claimed in claim 1 wherein said parasympatholytic agent is scopolamine butylbromide.

* * * * *